(12) United States Patent
Pierce et al.

(10) Patent No.: US 6,262,038 B1
(45) Date of Patent: Jul. 17, 2001

(54) GERMICIDAL COMPOSITION

(75) Inventors: Deborah Pierce, Walnut, CA (US); Timothy J. Heilman, Incline Valley, NV (US)

(73) Assignee: David Christal, Ltd., Las Vegas, NV (US)

( * ) Notice: Subject to any disclaimer, the term of this patent is extended or adjusted under 35 U.S.C. 154(b) by 0 days.

(21) Appl. No.: 09/284,687

(22) PCT Filed: Oct. 16, 1997

(86) PCT No.: PCT/US97/18630

§ 371 Date: Apr. 16, 1999

§ 102(e) Date: Apr. 16, 1999

(87) PCT Pub. No.: WO98/16192

PCT Pub. Date: Apr. 23, 1998

Related U.S. Application Data

(60) Provisional application No. 60/028,955, filed on Oct. 17, 1996.

(51) Int. Cl.$^7$ ............... A01N 43/04; A01N 31/00; A01N 37/00; A01N 41/02; A61L 2/16
(52) U.S. Cl. ............... 514/53; 422/28; 514/23; 514/25; 514/517; 514/529; 514/552; 514/557; 514/558; 514/559; 514/574; 514/708; 514/709; 514/711; 514/723; 514/729; 514/738; 514/880; 514/881; 514/975
(58) Field of Search ................... 514/22, 25, 53, 514/557, 574, 880, 881, 975, 23, 708, 709, 711, 517, 529, 552, 558, 559, 723, 729, 738; 422/28

(56) References Cited

U.S. PATENT DOCUMENTS

| 4,140,649 | 2/1979 | Bossert et al. | 426/286 |
|---|---|---|---|
| 4,404,040 | 9/1983 | Wang | 134/22.14 |
| 4,870,010 | 9/1989 | Hayes | 424/114 |
| 4,999,195 | 3/1991 | Hayes | 424/114 |
| 5,143,720 | 9/1992 | Lopes | 424/55 |
| 5,320,772 | 6/1994 | Tricca | 15/104.93 |
| 5,460,833 | 10/1995 | Andrews et al. | 424/606 |
| 5,490,992 | 2/1996 | Andrews et al. | 424/606 |
| 5,536,155 | * 7/1996 | Futaki et al. | 424/195.1 |

FOREIGN PATENT DOCUMENTS

WO 98/16192  4/1998  (WO).

OTHER PUBLICATIONS

Lang et al., Antimicrobial effects of biosurfactants (Fett Wiss. Technol. (1989), 91(9), 363–6), STN/CAS online, file CAPLUS, abstract.*

* cited by examiner

*Primary Examiner*—Jose' G. Dees
*Assistant Examiner*—Frank Choi
(74) *Attorney, Agent, or Firm*—Klarquist Sparkman Campbell Leigh & Whinston, LLP

(57) ABSTRACT

A germicidal composition suitable for cleaning fruits, vegetables, skin and hair, includes a mixture of fruit acids and a surfactant. The surfactant may be an anionic surfactant (such as sodium lauryl sulfate), a sophorose lipid biosurfactant, or a combination of the two surfactants. The mixture of fruit acids may include citric acid, glycollic acid, lactic acid, malic acid and tartaric acid. The fruit acids are preferably present, in an aqueous solution, in a sufficient amount to produce a pH of about 2–6, for example 3.8–4.2. The compositions of the present invention are germicidal, and are sufficient to kill 100% of *E. coli*, Salmonella and Shigelia in 30 seconds after application to the surface of the object.

14 Claims, No Drawings

GERMICIDAL COMPOSITION

This application is a 371 of PCT/US97/18630, filed on Oct. 16, 1997, and claims benefit of Provisional application 60/028,955, filed Oct. 17, 1996.

FIELD OF THE INVENTION

This invention concerns germicidal compositions, such as compositions useful for personal hygiene and home cleaning. In more particular embodiments, the invention is related to germicidal compositions for use in washing fruits and vegetables, and which is also suitable for cleaning skin and hair.

BACKGROUND OF THE INVENTION

Food borne pathogens and contaminants are a significant threat to public health. Recent fatal outbreaks of *Escherichia coli* infection following ingestion of infected food have publicized the severity of this public health problem. Other food borne pathogens that can cause gastroenteritis or systemic infection include *Salmonella typhi, Shigella dysenteriae, Campylobacter jejuni, Bacillus cereus, Clostridium perfringens*, the Hepatitis A virus, influenza viruses, adenoviruses, *Staphylococcus aureus*, and many others. Some of these organisms can be transmitted to food, such as fresh produce, during preparation or handling. Diseases caused by such pathogens are a significant public health problem.

Another problem with the consumption of fresh produce, such as fruits and vegetables, is that they are sometimes contaminated with soil and pesticides or other toxins. Some pathogens thrive in soil, hence dirt on food may transmit disease. Toxic contaminants in the dirt or on the food have been incriminated as a cause of acute enteric illnesses, and many consumers are concerned about long-term effects (such as carcinogenesis) from chronic ingestion of these toxins. This concern is a particular dilemma for health conscious individuals, whose diets often contain a high proportion of fresh fruits and vegetables.

Although consumption of fruits and vegetables has significant health advantages, these food items are often exposed to toxins (such as pesticides) during production. Moreover, fruits and vegetables are often handled by numerous people (from agricultural workers to consumers) in food distribution channels, which provides multiple opportunities for infection of the food with gastroenteric and other pathogens.

It is therefore an object of this invention to provide a composition and method which addresses this public health problem by inactivating pathogens and removing toxins from the surface of food items such as fruits and vegetables.

Another object of this invention is to inactivate or remove the pathogens or contaminants in an environmentally safe and biologically non-threatening manner.

Yet another object is to provide a germicidal composition that is useful in cleaning fomites, such as human hands and food preparation surfaces.

Finally, it is an object to provide such a composition that is not harmful to the human skin.

SUMMARY OF THE INVENTION

The foregoing objects are achieved by providing a biologically compatible, germicidal composition that is suitable for use as a fruit and vegetable wash. The composition includes a pH lowering agent in a sufficient amount to lower the pH of the composition to at least 6, and a surfactant, such as sodium lauryl sulfate or a sophorose lipid biosurfactant, in a germicidal amount sufficient to kill 100% of at least *E. coli, Salmonella typhi,* and *Shigella dysenteriae*, in 30 seconds at the pH of the composition. The pH lowering agent is preferably a biocompatible fruit acid, such as citric acid, glycollic acid, lactic acid, malic acid, or tartaric acid. In some embodiments, the fruit acid is a combination of two or more of these fruit acids, or a combination of all of them.

Other embodiments also include a second surfactant, such as a biosurfactant, to improve the emulsifying properties of the composition. In particular embodiments, the biosurfactant is a sophorose lipid biosurfactant prepared by fermentation of yeast. This biosurfactant has been found to provide additional antimicrobial activity, and has a moisturizing effect on human skin. Hence embodiments of the invention that contain biosurfactant are particularly suitable for formulations intended for use as skin and hair products.

In some embodiments, the composition includes a pH lowering agent comprising a mixture of fruit acids, sufficient to lower the pH of the composition to 2–5, or more specifically 3–6, most specifically 3.8–4.2; sodium lauryl sulfate in an amount of 1–20% by weight of the composition, more specifically 2–5% by weight; and a sophorose lipid biosurfactant in an amount of 0.1–2.0% by weight of the composition, more specifically 0.1–2.0%, most specifically about 0.3% by weight. Trace amounts of fragrants, such as a natural citrus complex, may be added to the composition to enhance its odor.

The invention also includes a method of cleaning fomites, comprising the steps of applying to the fomite a germicidally effective amount of the composition, and leaving the composition on the fomite for an effective period of time to kill 100% of organisms selected from the group consisting of *Escherichia coli, Salmonella typhi* and *Shigella dysenteriae*. The fomite is, for example, selected from the group consisting of fruits and vegetables, food preparation surfaces such as cutting boards and kitchen counters, doorknobs, human hands, human hair, eating utensils, and many other items.

The composition may be formulated as a liquid cleaning agent that can be poured from a bottle or sprayed from a spray pump. Alternatively, thickeners and/or moisturizers can be added to provide a formulation that is suitable for use as a hand lotion, shampoo, baby wipe, or makeup remover. The composition may also be used in household cleaners, a body wash, or hand towelettes.

The foregoing and other objects, features, and advantages of the invention will become more apparent from the following detailed description of a preferred embodiment which proceeds with reference to the accompanying drawings.

DETAILED DESCRIPTION OF A PREFERRED EMBODIMENT

In this specification, the amounts of ingredients in the composition are expressed as percentages by weight of the active ingredient.

The germicidal composition of this disclosed embodiment includes a mixture of a surfactant and a pH lowering agent that lowers the pH of the composition to 2–6. The surfactant is also germicidal, and is present in an amount that, in combination with the pH lowering agent, kills 100% of at least *E. coli, Salmonella typhi* and *Shigella dysenteriae* within 30 seconds of applying the composition to an infected surface. The composition may also have germicidal activity against a broad variety of pathogens listed in Example 4.

A particular disclosed surfactant that has this germicidal activity is sodium lauryl sulfate. Other surfactants would be sodium laureth sulfate, ammonium lauryl sulfate, ammonium laureth sulfate, or a biosurfactant such as a sophorose biosurfactant. A specific pH lowering agent is one or more fruit derived acids.

In particular embodiments, the range of sodium lauryl sulfate would be about 1–20% by weight, more particularly about 2–5% by weight, and most particularly about 4.5% by weight. The fruit acids would be added in a sufficient amount to provide a composition having a pH of about 2–6, more particularly 3–5, or more particularly 3.8–4.2. A weight ratio of the surfactant active ingredient (such as sodium lauryl sulfate) to the active ingredients of the fruit acids is about 1:1 to 3:1, more specifically about 2:1. When the sodium lauryl sulfate is present in an amount of about 4.5% by weight of the active ingredient, then the fruit acids would be provided in an amount of about 2.3% by weight. In such specific embodiments, the ratio of sodium lauryl sulfate to fruit acids (by weight) is about 2:1. The remainder of the composition may be an inert carrier, such as deionized water, although additional thickeners, sudsing agents, preservatives, additional germicidal agents, and other materials may also be added.

In yet other embodiments, the germicidal composition comprises sodium lauryl sulfate in an amount of about 4–5%; ionic sophorose lipid surfactants in an amount of less than about 1%; and a mixture of fruit acids in an amount of about 2–3%, wherein the mixture of fruit acids includes citric acid, glycollic acid, lactic acid, malic acid and tartaric acid; and a sufficient amount of water so that the pH of the composition is about 3–5, more particularly 3.8.

The sodium lauryl sulfate used with the present invention may be obtained, for example, from Chemron Corporation of Paso Robles, Calif., under product designation Sulfochem SLC. This product has a pH of about 7.5–8.5, a density of 8.84, and a specific gravity of 1.06.

The pH lowering agents of the composition are fruit extracts containing natural fruit acids, preferably alpha-hydroxy fruit acids. Although the natural fruit extracts are preferred, synthetic fruit acids or analogs may be used. In the examples disclosed below, the fruit acids are a mixture of citric acid, glycollic acid, lactic acid, malic acid, and tartaric acid. These fruit acids are commercially available. For example, a mixture of alpha-hydroxy fruit acid extracts can be obtained from Brooks Industries of South Plainfield, N.J. under the trade name MULTIFRUIT BSC (product code #6033). The chemical structures and composition of the MULTIFRUIT extract are shown in the accompanying Tables 1–2.

TABLE 1

ALPHA-HYDROXY FRUIT ACIDS IN MULTIFRUIT EXTRACT $$\begin{array}{c} CH_2-COOH \\ | \\ HO-C-COOH \\ | \\ CH_2-COOH \end{array}$$

Citric Acid $HO-CH_2-COOH$

Glycolic Acid

TABLE 1-continued

ALPHA-HYDROXY FRUIT ACIDS IN MULTIFRUIT EXTRACT $$\begin{array}{c} CH_3-CH-COOH \\ | \\ OH \end{array}$$

Lactic Acid $$\begin{array}{c} HO-CH-COOH \\ | \\ CH_2-COOH \end{array}$$

Malic Acid $$\begin{array}{c} HO-CH-COOH \\ | \\ HO-CH-COOH \end{array}$$

Tartaric Acid

TABLE 2

MULTIFRUIT EXTRACT

| INGREDIENTS | Percent (%) |
|---|---|
| LACTIC ACID | 28–32% |
| GLYCOLLIC ACID | 12–17% |
| CITRIC ACID | 2–6% |
| WATER | 40% APPROX |
| MALIC/TARTARIC ACID | 2% APPROX |

Sophorose lipids are used as biosurfactants in some embodiments of the composition, particularly when it is desired to provide a more comfortable, fatty texture to the product. Sophorose lipids are available as either non-ionic or anionic biosurfactants prepared by fermentation of *Candida Bombicola* in a substrate of glucidic acid and vegetables oils. These lipids are glycolipids, containing a disaccharide glyco moiety, linked to a fatty chain by a glycosidic linkage. The sophorose lipids have good emulsifying abilities, and are compatible with cosmetic ingredients such as vegetable and mineral oils, surfactants, alcohols, viscosity modifiers (such as cellulose and gums), and wetting agents (such as sorbitol, glycerine, propylene glycol), that make them ideal for use of the present antimicrobacterial composition in cosmetics (such as lipsticks and foundations), and other personal care products, such as shampoos, hair gels, creams, sun lotions, deodorants, and toothpastes.

Also included within the scope of this invention are functionalized sophorose lipids, such as oleyl sophorose lipids and propylene oxide sophorose lipids. These biosurfactants have specific compatibility with the skin, and are quite moisturizing.

Specific examples of sophorose lipids suitable for incorporation into the composition of the present invention are shown below, and can be obtained from Soliance of Pomacle, France, or through Tri-K Industries, Inc. of Emerson, N.J.

NON IONIC SOPHOROSE-LIPIDS

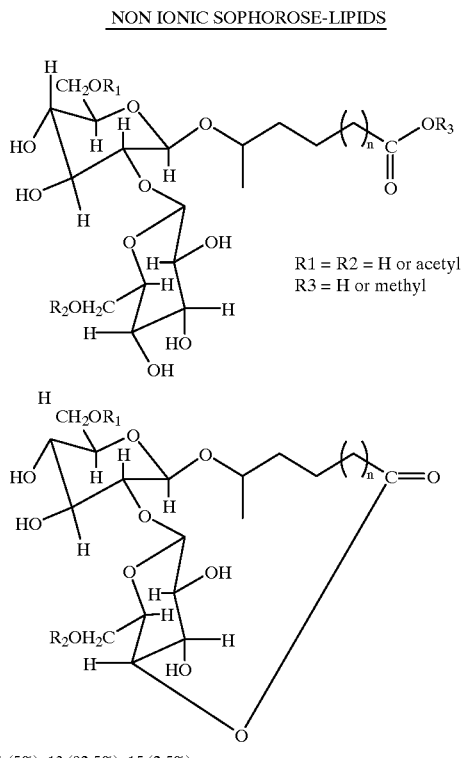

R1 = R2 = H or acetyl
R3 = H or methyl n = 11 (5%), 13 (92.5%), 15 (2.5%)

ANIONIC SOPHOROSE-LIPIDS

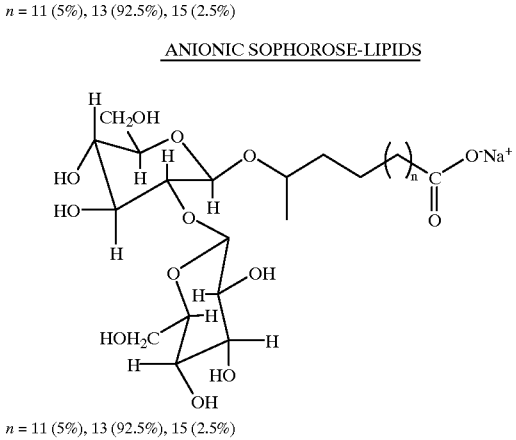

n = 11 (5%), 13 (92.5%), 15 (2.5%)

An example of a specific formulation of the composition that includes the sophorose lipids is:

| Ingredient | Weight |
|---|---|
| Deionized water: | 92.9% |
| Sodium lauryl sulfate | 4.5% |
| Sophorose Lipids | 0.3% |
| Fruit Acids | 2.3% |

The sophorose lipids may be present in the germicidal composition of the present invention in an amount of at least 0.1%, for example 0.1–5.0%, more specifically 0.1–2.0%, and even more particularly 0.1–0.3%.

The following examples provide additional information about the manufacture and use of specific germicidal compositions in accordance with the present invention.

EXAMPLE 1

This example provides specific information about a process of manufacturing an organic fruit wash in accordance with the present invention. The composition of the fruit wash in this example is:

| Ingredient | weight % |
|---|---|
| Deionized Water | 82.38 |
| Sodium Lauryl Sulfate 30% (30% by wt SLS) | 15.00 |
|  | (4.5% SLS) |
| Sophorose Lipids-Ionic | 0.30 |
| Multifruit BSC | 2.30 |
| Natural Citrus Complex 3788-10012B | 0.025 |
|  | 100.00 |

In a specific example, 82 lbs of water would be introduced into a mixing tank, and mixing started. Then sodium lauryl sulfate (SLS) would be added in an amount of 15 lbs of a 30% SLS solution, and heated to 42–50° C. while mixing continues. When the mixture reaches the desired temperature, 0.3 lbs of ionic sophorose lipids (99% of the total amount of lipid to be added) is added to the mixture while mixing continues. The mixture is then cooled toward 32° C. When the temperature is 40° C. or less, 2.3 lbs of the multifruit BSC is added to the mixture, and all ingredients are mixed in solution until the batch is homogenous.

In a separate container, the remaining 1% of the sophorose lipid is mixed with 0.025 lbs of the natural citrus complex and added to the batch. Mixing is continued until the batch temperature reaches 35° C. The mixture is then pumped to a storage tank through a 40 mesh screen filter to remove any particulate contaminants.

The resulting product is a clear water white liquid having a citrus odor, a pH at 25° C. of 3.8–4.2, and a water thin viscosity with a specific gravity of about 1.008.

EXAMPLE 2

The germicidal composition of Example 1 can also be made without the sophorose lipids. In this case, the manufacturing steps of Example 1 are followed except the sophorose lipids are not added. A specific example of a composition formulation made in accordance with this example is:

| Ingredient | weight % |
|---|---|
| Sodium lauryl sulfate | 4.5 |
| Fruit acids | 2.3 |
| Deionized water | 93.2 |
|  | 100.00 |

EXAMPLE 3

Germicidal activity of various formulations were determined by a log reduction assay, which determined the effectiveness of the formulation at reducing a microorganism population. The following test organisms were used with this assay (ATCC accession numbers appear in parentheses):

*Escherichia coli* (ATCC 8739)
*Salmonella typhi* (ATCC 6534)

*Shigella dysenteriae* (ATCC 6539 and 13313)

The organisms were supplied as Culti-Loops and maintained as recommended by the vendor of the culture collection.

The culture medium used was trypticase soy agar with lecithin and polysorbate 80 (TSA). The surface of TSA slants were inoculated with each of the organisms, and the bacterial cultures were incubated at 30–35° C. for 18–24 hours. Following the incubation period, the slant was washed with 3.0 ml of sterile phosphate buffered saline (PBS) to harvest bacterial growth. The microbial count was adjusted to approximately $10^8$ organisms using a spectrophotometer.

Then 20 ml of test product was introduced into sterile centrifuge tubes. A 1:10 dilution of the prepared bacterial stock suspension was adjusted to contain approximately $10^7$ organisms. Then 0.2 ml of this diluted bacterial stock was inoculated into the 20 ml test product in the sterile tube. This inoculum was approximately $10^5$ organisms.

At intervals of 30 seconds, 1 minute and 5 minutes, a 1.0 ml sample was taken from each tube and put into 9.0 ml of D/E neutralizing broth (1:10 dilution). Dilution was continued in series with D/E broth to achieve countable plates per time point (1:10, 1:100, and 1:1000). The dilutions were plated in sterile petri dishes and covered with TSA. The plates were then incubated at 35° C. for 48 hours.

As a control, a separate tube containing 20 ml of sterile PBS was inoculated with each organism. The same test procedure was performed as with the test product.

After the incubation period, all plates were counted to achieve final counts per time accounting for dilution factors. Plates with no growth were scored as less than 10 colony forming units per ml (CFU/ml). Plate counts were determined from the adjusted bacterial stock suspensions to determine the initial count. At each of the three time points, the percent reduction of bacterial growth was calculated by the following formula:

$$\frac{\text{Initial Count} - \text{Count at Time Interval}}{\text{Initial Count}} \times 100$$

Log reduction was then assessed as follows:

1 Log reduction=90.0% reduction

2 Log reduction=99.0% reduction

3 Log reduction=99.9% reduction

The results of these assays are shown in the following Table 3–6.

TABLE 3

Sodium Lauryl Sulfate Solution Only

| EXPOSURE TIME | CONCENTRATION OF ORGANISM CFU/ml | | % REDUCTION | | LOG REDUCTION | |
|---|---|---|---|---|---|---|
| | Control | Product | Control | Product | Control | Product |
| *Escherichia coli* (ATCC 8739) | | | INITIAL INOCULUM $3.10 \times 10^6$ CFU/ml | | | |
| 30 SEC | $3.00 \times 10^6$ | $1.30 \times 10^5$ | 3.23% | 96.81% | 0.014 | 1.38 |
| 1 MIN | $2.60 \times 10^6$ | $8.10 \times 10^4$ | 16.13% | 97.39% | 0.76 | 1.58 |
| 5 MIN | $2.30 \times 10^6$ | $6.90 \times 10^4$ | 25.81% | 97.77% | 0.13 | 1.65 |
| *Salmonella typhi* (ATCC 6534) | | | INITIAL INOCULUM $3.10 \times 10^6$ CFU/ml | | | |
| 30 SEC | $3.00 \times 10^6$ | $1.20 \times 10^5$ | 3.23% | 96.13% | 0.014 | 1.41 |
| 1 MIN | $2.70 \times 10^6$ | $1.10 \times 10^5$ | 12.90% | 96.45% | 0.60 | 1.45 |
| 5 MIN | $2.30 \times 10^6$ | $9.00 \times 10^4$ | 25.81% | 97.10% | 0.13 | 1.54 |

TABLE 3-continued

Sodium Lauryl Sulfate Solution Only

| EXPOSURE TIME | CONCENTRATION OF ORGANISM CFU/ml | | % REDUCTION | | LOG REDUCTION | |
|---|---|---|---|---|---|---|
| | Control | Product | Control | Product | Control | Product |
| *Shigella dysenteriae* (ATCC 6539) | | | INITIAL INOCULUM $3.20 \times 10^6$ CFU/ml | | | |
| 30 SEC | $2.50 \times 10^6$ | $1.20 \times 10^5$ | 21.88% | 96.25% | 0.11 | 1.43 |
| 1 MIN | $2.30 \times 10^6$ | $9.10 \times 10^4$ | 28.13% | 97.16% | 0.14 | 1.55 |
| 5 MIN | $2.10 \times 10^6$ | $5.20 \times 10^4$ | 34.38% | 98.38% | 0.18 | 1.79 |

TABLE 4

Multiple-Fruit Acid Solution Only

| EXPOSURE TIME | CONCENTRATION OF ORGANISM CFU/ml | | % REDUCTION | | LOG REDUCTION | |
|---|---|---|---|---|---|---|
| | Control | Product | Control | Product | Control | Product |
| *Escherichia coli* (ATCC 8739) | | | INITIAL INOCULUM $3.10 \times 10^6$ CFU/ml | | | |
| 30 SEC | $3.00 \times 10^6$ | $1.80 \times 10^5$ | 3.23% | 94.19% | 0.014 | 1.24 |
| 1 MIN | $2.60 \times 10^6$ | $1.70 \times 10^5$ | 16.13% | 94.52% | 0.76 | 1.26 |
| 5 MIN | $2.30 \times 10^6$ | $6.90 \times 10^4$ | 25.81% | 94.84% | 0.13 | 1.29 |
| *Salmonella typhi* (ATCC 6534) | | | INITIAL INOCULUM $3.10 \times 10^6$ CFU/ml | | | |
| 30 SEC | $3.00 \times 10^6$ | $1.50 \times 10^5$ | 3.23% | 95.16% | 0.014 | 1.32 |
| 1 MIN | $2.70 \times 10^6$ | $1.40 \times 10^5$ | 12.90% | 95.48% | 0.60 | 1.35 |
| 5 MIN | $2.30 \times 10^6$ | $9.60 \times 10^4$ | 25.81% | 96.90% | 0.13 | 1.51 |
| *Shigella dysenteriae* (ATCC 6539) | | | INITIAL INOCULUM $3.20 \times 10^6$ CFU/ml | | | |
| 30 SEC | $2.50 \times 10^6$ | $1.50 \times 10^5$ | 21.88% | 95.31% | 0.11 | 1.33 |
| 1 MIN | $2.30 \times 10^6$ | $1.10 \times 10^5$ | 28.13% | 96.56% | 0.14 | 1.46 |
| 5 MIN | $2.10 \times 10^6$ | $8.10 \times 10^4$ | 34.38% | 97.47% | 0.18 | 1.60 |

TABLE 5

Sodium Lauryl Sulfate + Fruit Acids + Natural Citrus Complex

| EXPOSURE TIME | CONCENTRATION OF ORGANISM CFU/ml | | % REDUCTION | | LOG REDUCTION | |
|---|---|---|---|---|---|---|
| | Control | Product | Control | Product | Control | Product |
| *Escherichia coli* (ATCC 8739) | | | INITIAL INOCULUM $3.70 \times 10^6$ CFU/ml | | | |
| 30 SEC | $3.60 \times 10^6$ | <10 | 2.70% | 100% | 0.01 LOG | 6 LOG |
| 1 MIN | $3.10 \times 10^6$ | <10 | 16.22% | 100% | 0.08 LOG | 6 LOG |
| 5 MIN | $2.70 \times 10^6$ | <10 | 27.03% | 100% | 0.14 LOG | 6 LOG |
| *Salmonella typhi* (ATCC 6534) | | | INITIAL INOCULUM $3.70 \times 10^6$ CFU/ml | | | |
| 30 SEC | $2.30 \times 10^6$ | <10 | 37.84% | 100% | 0.21 LOG | 6 LOG |
| 1 MIN | $2.20 \times 10^6$ | <10 | 40.54% | 100% | 0.23 LOG | 6 LOG |
| 5 MIN | $2.00 \times 10^6$ | <10 | 45.95% | 100% | 0.27 LOG | 6 LOG |
| *Shigella dysenteriae* (ATCC 6539) | | | INITIAL INOCULUM $2.40 \times 10^6$ CFU/ml | | | |
| 30 SEC | $1.80 \times 10^6$ | <10 | 25.00% | 100% | 0.12 LOG | 6 LOG |

TABLE 5-continued

Sodium Lauryl Sulfate + Fruit Acids + Natural Citrus Complex

|  | CONCENTRATION OF ORGANISM CFU/ml | | % REDUCTION | | LOG REDUCTION | |
|---|---|---|---|---|---|---|
| EXPOSURE TIME | Control | Product | Control | Product | Control | Product |
| 1 MIN | 1.70 × 10⁶ | <10 | 29.17% | 100% | 0.15 LOG | 6 LOG |
| 5 MIN | 2.40 × 10⁶ | <10 | 41.67% | 100% | 0.23 LOG | 6 LOG |

TABLE 6

Sodium Lauryl Sulfate + Fruit Acids + Natural Citrus Complex + Biosurfactant

|  | CONCENTRATION OF ORGANISM CFU/ml | | % REDUCTION | | LOG REDUCTION | |
|---|---|---|---|---|---|---|
| EXPOSURE TIME | Control | Product | Control | Product | Control | Product |
| *Escherichia coli* (ATCC 8739) | INITIAL INOCULUM 2.40 × 10⁶ CFU/ml | | | | | |
| 30 SEC | 2.10 × 10⁶ | <10 | 12.50% | 100% | 0.06 LOG | 6 LOG |
| 1 MIN | 2.00 × 10⁶ | <10 | 16.67% | 100% | 0.08 LOG | 6 LOG |
| 5 MIN | 1.80 × 10⁶ | <10 | 25.00% | 100% | 0.12 LOG | 6 LOG |
| *Salmonella typhi* (ATCC 6534) | INITIAL INOCULUM 3.40 × 10⁶ CFU/ml | | | | | |
| 30 SEC | 3.20 × 10⁶ | <10 | 5.88% | 100% | 0.03 LOG | 6 LOG |
| 1 MIN | 2.70 × 10⁶ | <10 | 20.59% | 100% | 0.10 LOG | 6 LOG |
| 5 MIN | 2.10 × 10⁶ | <10 | 38.24% | 100% | 0.21 LOG | 6 LOG |
| *Shigella dysenteriae* (ATCC 6539) | INITIAL INOCULUM 2.90 × 10⁶ CFU/ml | | | | | |
| 30 SEC | 2.70 × 10⁶ | <10 | 6.90% | 100% | 0.03 LOG | 6 LOG |
| 1 MIN | 2.60 × 10⁶ | <10 | 10.34% | 100% | 0.05 LOG | 6 LOG |
| 5 MIN | 2.00 × 10⁶ | <10 | 31.03% | 100% | 0.16 LOG | 6 LOG |

The data in Table 3 demonstrate that sodium lauryl sulfate solution alone reduces bacterial growth by only about 96–97% at 30 seconds, 96–97% at 1 minute, and 97–98% at five minutes. The multifruit solution alone (containing a mixture of fruit acids) only reduces bacterial growth by 94–97% (Table 4). The combination of sodium lauryl sulfate and fruit acids (including a natural citrus complex) reduces bacterial growth by 100%, for all the bacteria tested (Table 5). This 100% reduction of bacterial growth is considered "germicidal." A "germicidal" composition, as that term is used in this specification, means that 100% of a pathogen (such as bacteria) are killed at 30 seconds. Germicidal activity can be determined using the method described in Example 3.

The germicidal composition made in accordance with Example 1, which included sodium lauryl sulfate, fruit acids, biosurfactant and citrus complex (Table 6), also showed 100% reduction of live bacteria at 30 seconds, 1 minute, and 5 minutes.

These Examples demonstrate that germicidal activity is not achieved with either sodium lauryl sulfate or a mixture of fruit acids alone. The combination of the surfactant and fruit acids, however, is shown to provide germicidal activity. Germicidal activity is achieved without the biosurfactant, but the presence of the biosurfactant was not observed to diminish germicidal activity.

Although germicidal activity could not be determined sooner than 30 seconds after exposure, germicidal activity is believed to occur almost instantaneously upon exposure to the bactericidal composition. Removal of toxics also occurs almost instantly as soon as the toxics (such as pesticide residuum) are solubilized in the composition.

EXAMPLE 4

The assays of Example 3 demonstrate that the composition has germicidal activity against three specific gastroenteric pathogens (which are pathogens that cause infection and illness of the stomach, intestines, or both): *E. coli*, *Salmonella typhi*, and *Shigella dysenteriae*. However, the composition can be used to prevent the growth of or kill a broad variety of pathogens, selected from the group consisting of at least bacteria, viruses, fungi and mycoplasma.

Examples of bacteria that the composition has bacteriostatic or bactericidal activity against include a broad variety of gram positive and gram negative bacteria, including *Streptococcus pyogenes, Streptococcus pneumoniae, Staphylococcus aureus, S. viridans, S. epidernidis, Pseudomonas aeruginosa, Klebsiella pneumoniae, Hemophilus influenza, Chlamydia trachomatis, Proteus mirabilis, Proteus vulgaris, Vibrio cholera* (for example serotype 01), *Campylobacter jejuni,* and *Helicobacter pylori.*

Examples of viruses that the composition has germistatic or germicidal activity against include enteroviruses, adenoviruses, rhinoviruses, norwalk virus, respiratory syncytial virus (RSV), rotavirus, and hepatitis viruses such as hepatitis A, herpes simplex I and II, and influenza virus.

The composition of the present invention can also be used to prevent or eliminate viable organisms selected from the group consisting of Cryptosporidium and *Mycoplasma pneumoniae,* and fungi such as Candida, for example *Candida albicans.*

EXAMPLE 5

The composition can be used in a method of eliminating viable pathogens on fomites. A fomite is an object, that is not in itself harmful, but that is able to harbor pathogenic microorganisms, and thus may serve as an agent of disease transmission. Examples of fomites include human hands, food preparation surfaces, and the surfaces of fruits, vegetables and other foods. The method includes applying an effective amount of the composition to the fomite, and leaving it on the fomite for a sufficient period of time to have a germicidal activity. This period of time is usually almost immediately, once the composition is placed on the object. Toxins (such as residual pesticides) are also immediately removed. In some embodiments, it may be preferred to leave the composition in contact with the fomite 30 seconds or less, or 1 minute or less, or 5 minutes or less.

In particular reference to fruits and vegetables, the composition of Example 2 can be sprayed or poured on the surface of the fruit or vegetable. A vegetable brush can optionally be used to spread the composition on the food product if dirt is embedded in the surface. The product can alternatively be immersed in the composition. The composition is ideally spread to substantially cover the surface of the vegetable for a sufficient period of time, for example, 30 seconds, 1 minute, or even 5 minutes or longer. The product is then washed, for example with water, to remove the composition and any toxins or other unwanted material on the surface of the food.

Having illustrated and described the principles of the invention in several preferred embodiments, it should be apparent to those skilled in the art that the invention can be modified in arrangement and detail without departing from such principles. We claim all modifications coming within the spirit and scope of the following claims.

What is claimed is:

1. A germicidal composition comprising:
   a mixture of alpha-hydroxy fruit acids in an amount of 2–3% by weight of the composition, and which is sufficient to lower the pH of the composition to 2–6;
   sodium lauryl sulfate in an amount of 1–20% by weight of the composition;
   a sophorose lipid biosurfactant in an amount of 0.1–2.0% by weight of the composition.

2. The composition of claim 1, wherein the fruit acids are present in an amount of about 2.3% by weight of the composition, the sodium lauryl sulfate is present in an amount of about 4.5% by weight of the composition, and the sophorose lipids are present in an amount of about 0.3% by weight of the composition.

3. The composition of claim 2, wherein the mixture of fruit acids comprises citric acid, glycollic acid, lactic acid, malic acid and tartaric acid.

4. The composition of claim 1, wherein the weight ratio of the sodium lauryl sulfate to the fruit acids is about 1:1 to 3:1.

5. The composition of claim 4, wherein the ratio of sodium lauryl sulfate to the fruit acids is about 2:1.

6. A germicidal composition, comprising:
   sodium lauryl sulfate in an amount of about 4–5% by weight of the composition;
   ionic sophorose lipid surfactants in an amount of less than about 1% by weight of the composition;
   a mixture of fruit acids in an amount of about 2–3% by weight of the composition, wherein the mixture of fruit acids comprises citric acid, glycollic acid, lactic acid, malic acid and tartaric acid;
   sufficient water to bring the pH of the composition to about 3–5.

7. The composition of claim 6, wherein the pH of the composition is about 3.8–4.2.

8. The composition of claim 6, wherein the sodium lauryl sulfate is present in an amount of about 4.5% by weight of the composition.

9. The composition of claim 6, wherein the mixture of fruit acids is present in an amount of about 2.3% by weight of the composition.

10. A germicidal composition, comprising:
    sodium lauryl sulfate surfactant in an amount of about 4.5% by weight of the composition;
    ionic sophorose lipid surfactant in an amount of about 0.30% by weight of the composition;
    a mixture of fruit acids in an amount of about 2.3% by weight of the composition, wherein the mixture of fruit acids comprises citric acid, glycollic acid, lactic acid, malic acid and tartaric acid, and the weight ratio of the surfactants to the mixture of fruit acids is about 2:1; and
    sufficient water to bring the pH of the composition to about 3.8–4.2.

11. A method of cleaning fomites, comprising the steps of:
    applying to the fomite a germicidally effective amount of the composition of claim 1, and leaving it on the fomite for an effective period of time to kill bacterial pathogens on the fomite.

12. The method of claim 11, wherein the fomite is fruit or vegetables.

13. The method of claim 11, wherein the fomite is skin or hair.

14. A method of cleaning fomites, comprising the steps of:
    applying to the fomite a germicidally effective amount of the composition of claim 10, and leaving the composition on the fomite for as briefly as 30 seconds to kill 100% of organisms selected from the group consisting of *Escherichia coli*, Salmonella and Shigella.

* * * * *